United States Patent [19]
Nunez

[11] 4,406,653
[45] Sep. 27, 1983

[54] ADHESIVELY MOUNTED CATHETER BALLOON

[75] Inventor: Chris E. Nunez, Garden Grove, Calif.

[73] Assignee: Critikon, Inc., Tampa, Fla.

[21] Appl. No.: 342,873

[22] Filed: Jan. 26, 1982

[51] Int. Cl.³ ............................................. A61M 25/00
[52] U.S. Cl. .................................................. 604/103
[58] Field of Search ............... 128/129, 246, 325, 344, 128/348, 349 E, 349 BV; 156/191, 192, 193, 194, 304.1, 304.2; 604/97–103

[56] References Cited

U.S. PATENT DOCUMENTS

| | | | |
|---|---|---|---|
| 3,503,399 | 3/1970 | Ettman et al. | 128/349 B |
| 3,884,242 | 5/1975 | Bazell et al. | 128/349 B |
| 4,003,382 | 1/1977 | Dyke | 604/97 |
| 4,168,710 | 9/1979 | Rosenberg | 128/246 |
| 4,259,960 | 4/1981 | Taylor | 128/349 B |

Primary Examiner—Richard J. Apley
Assistant Examiner—George Yanulis
Attorney, Agent, or Firm—Audley A. Ciamporcero, Jr.; Mark A. Hofer

[57] ABSTRACT

Provided is a method as well as apparatus for a catheter catheter-balloon assembly wherein the catheter balloon is mounted on the catheter by means of adhesive and, in the preferred mode, an annular internal rib protrusion of the catheter balloon is provided for forming a sharply defined boundary of adhesive thereby aiding in the even and symmetrical inflation of the catheter balloon.

1 Claim, 3 Drawing Figures

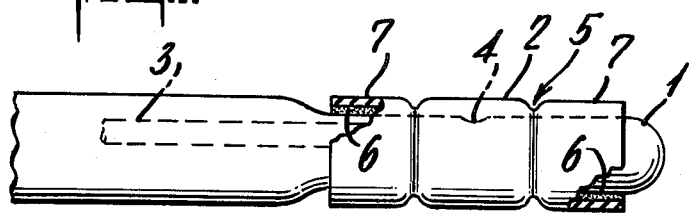
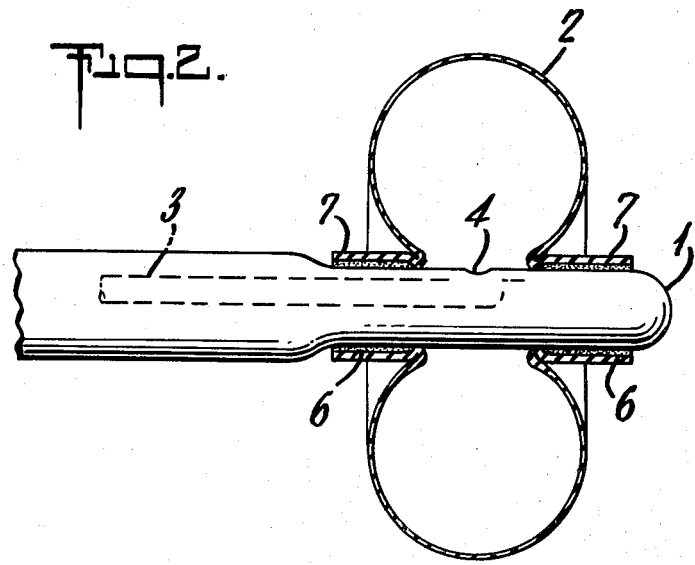
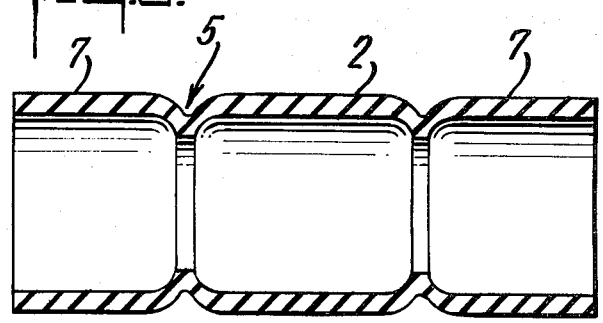

ADHESIVELY MOUNTED CATHETER BALLOON

FIELD OF THE INVENTION

This invention relates generally to the field of catheter balloons and specifically to those which are mounted on the catheter by means of adhesive.

BACKGROUND OF THE INVENTION

Catheters may be generally described as long flexible tubes having at least one continuous lumen running from end to end. The first catheters were used primarily as a means for emptying the bladder and although catheters are still extensively used for this purpose, in general, there have been many advances in the art of catheter production which have thereby permitted numerous alternative uses.

Catheters may now be obtained in multi-lumen form greatly expanding their potential usefulness. For instance, a typical catheter presently available provides for four individual and separate continuous lumens throughout the entire length of the catheter. Such a catheter, typically several feet long, may be inserted in a perpheral artery, typically in humans in the femoral artery at the groin region of a body to a sufficient extent so that the tip of the catheter rests in a region of the aorta close to the left ventricle or main pumping portion of the heart. In this location, numerous parameters of cardiac action may be monitored. For instance, installed at the tip of the catheter may be a solid state pressure transducer capable of responding to the hydraulic pressure changes resulting from the pumping action of the left ventricle. Signals from such a transducer are carried by thin leads in a separate lumen of the catheter. Similarly, the pressure transducer may be a chemically sensitive transducer capable of measuring oxygen or other gas partial pressures. Additionally, the catheter may have a separate lumen, generally of a larger bore diameter, adapted for the removal of a blood sample for later in vitro analysis.

An important parameter describing heart performance is cardiac output which refers to the volume-rate of blood pumped by the heart and is the product of the stroke volume and the heart rate. Cardiac output is generally expressed in terms of liters per minute. Calculation of the cardiac output therefore requires the prerequisite determination of the stroke volume. The indicator dilution technique has found widespread application in the determination of stroke volume. The technique involves the injection of a precise amount of dye or radioactive isotope containing solution having a known concentration. Subsequent removal of a known volume, after mixing, and the determination of the concentration of the dye in that sample will allow the calculation of the volume diluting material or blood in this case. The injection of such an indicator solution is generally accomplished by having a separate lumen within the catheter operated in conjunction with the sample withdrawal lumen.

Still yet another lumen may be incorporated in the catheter for the purposes of air conduction to inflate a normally collapsed sleeve typically installed at or near the tip of the catheter. Such a sleeve, when inflated, forms a balloon whose volume may be regulated by the amount of air used to inflate and the size of the sleeve installed. Regulation of the appropriate dimensions may therefore permit the complete occlusion of the vessel or partial occlusion as desired. Typically, the resilient material employed is a latex and referred to as a catheter baloon. The catheter balloon finds its utility primarily in two notable instances. It aids in the timing of dye injection and sample acquisition in the previously described indicator dilution technique, as well as a cardiac output assistance device. The latter, although still primarily in its experimental stages, employs complex instrumentation for purposes of timing the inflation of the catheter balloon with relation to the left ventricular contraction in order to maximize cardiac output.

In an effort to meet the demand for balloon catheters, several methods of manufacture have historically been employed. At present, all generally use some combination of three basic attachment techniques for mounting a resilient material in an air-tight sealing fashion to a catheter. Generally, these methods involve the use of adhesive means, clamping means by either a single solid clamp or by whipping with a thread type material or, some combination of these. Thus, the end of the tube of a balloon material may be mounted and sealed against the surface of the catheter by multiple windings of a thread which may or may not have a coating of adhesive. The windings may be on the outside of the balloon material or may be within a fold of the balloon material and in some cases, manufacturers have employed both methods in the attachment of their balloons to the catheter. Attachment of the balloon to the catheter by adhesive has been typically accomplished by application of the adhesive to the junction between the balloon and the catheter generally at the end of the balloon. The width of the adhesive bond has been largely regulated by the quantity of adhesive applied and the extent of "wicking" by capillary forces.

Consequently, application of the adhesive has not been accomplished without difficulty since typically, the adhesive is wicked to different extents between the balloon and the catheter resulting in an uneven adhesive bond boundary. Thus, the adhesive may form an uneven boundary in that it fails to form an annular ring, sharply demarcating the adhesive boundary, that is perpendicular to the longitudinal axis of the catheter and balloon. The result of such a non-square glue line is an uneven and often off center balloon following inflation. Such an unevenly inflated balloon is not only prone to greater mechanical failure due to large and uneven stress distributions, but also results in errors during data acquisition modes.

It is an object of the present invention to eliminate these problems associated with uneven adhesive boundaries by insuring that the adhesive bond forms a sharply defined annular boundary that is substantially perpendicular to the longitudinal axis of the catheter.

SUMMARY OF THE INVENTION

In accordance with the objects of the invention, there is provided a catheter balloon composed of a resilient material adhesively attached to a catheter in a sealing airtight fashion such that a sharply defined boundary of adhesive is formed by annular means. The annular means may be an annular ridge protruding from the surface of the catheter but preferably will be an annular internal rib-type protrusion of the resilient material making up the catheter balloon itself.

BRIEF DESCRIPTION OF THE DRAWINGS

Further unerstanding as well as other objectives of the invention will become clear upon analysis of the drawings wherein:

FIG. 1 is a side view of a balloon catheter employing the present invention in a non-inflated state;

FIG. 2 is a side view of a balloon catheter employing the present invention in an inflated state;

FIG. 3 is a cross-sectional view of the preferred balloon construction prior to its installation onto a catheter.

BEST MODE FOR CARRYING OUT THE INVENTION

Balloon material may be made from any resilient biocompatible material; typically natural latexes are preferred. Suitable latexes may be obtained from Goodrich and Heveatex and by procedures well known are generally compounded with different materials in order to appropriately adjust cure times. Typically, the latex is formed into a tubular structure having a thickness of approximately 0.010 plus or minus 0.0005 inches by dipping a mandrel into the liquid latex solution. As the latex cures on the mandrel, it forms a long tube which may thereafter be peeled off and cut to the appropriate length. Conventional methods have used smoothly cylindrical mandrels resulting in an equally smooth walled balloon.

With reference to FIG. 3, the present invention envisions the production of a balloon having preferably an snnular internal rib 5 disposed at some distance from the end 7. This may be easily produced by machining grooves on the surface of the mandrel so that during the dipping, the latex fills the groove thus forming the protruding rib. As the latex cures, the outer surface generally shows an indentation corresponding to and as a result of the rib formed on the inner surface.

FIG. 1 depicts the attachment of a balloon employing the rib feature on the end of a catheter 1 having an orifice 4 through which air for inflation of a balloon 2 may be pumped through the lumen 3. The balloon 2 is permanently affixed in sealing fashion to the catheter 1 by application of adhesive 6 at the ends 7 of the balloon 2. The adhesive is typically applied by rolling the end 7 of the resilient balloon material back onto itself towards the center of the expansion area, applying a layer of adhesive in annular fashion around the catheter 1 and then unrolling the end 7 of the balloon to cover the adhesive so applied. As the end is unrolled onto the adhesive, adhesive is forced to evenly wet the surfaces of the catheter and the balloon and is prevented from travelling further from the end 7 by rib protrusion 5. As a result, rib 5 acts to form a clear, sharp annular boundary of adhesive that is substantially perpendicular to the longitudinal axis of the catheter.

The sharp boundary of adhesive formed by the rib means 5 results in a substantially more even and predictable expansion of the balloon 2 as seen in FIG. 2. Deflation of the balloon is accomplished by withdrawing the air through orifice 4 and lumen 3.

The same sharp annular boundary of the adhesive may be alternatively accomplished by employing a ridge protruding from the surface of the catheter in the appropriate location. Economics and ease of balloon installation would, however, indicate the balloon to be the preferred site for the rib.

Still further alternatives may be readily appreciated by one skilled in the art without departing from either the spirit or the scope of the present invention.

I claim:

1. In a balloon catheter assembly employing an elongated catheter having a lumen communicating through an inflation port with an inflatable balloon member, the improvement wherein said balloon member is formed as an elongated elastomeric tube which in uninflated condition has three respective annular segments separated by a pair of respective inwardly extending annular ridges, a central one of said annular segments being inflatable and overlaying said port of said catheter, and said other two segments being adhesively attached to said catheter, wherein said ridges form well defined boundaries between respective adjacent attached and unattached segments of said balloon member.

* * * * *